United States Patent [19]
Rheiner

[11] 3,947,456

[45] Mar. 30, 1976

[54] SUBSTITUTED 4-PHENYL ISOQUINOLINES

[75] Inventor: Alfred Rheiner, Basel, Switzerland

[73] Assignee: Hoffman-La Roche Inc., Nutley, N.J.

[22] Filed: June 1, 1973

[21] Appl. No.: 365,921

Related U.S. Application Data

[62] Division of Ser. No. 102,551, Dec. 29, 1970, abandoned.

[30] Foreign Application Priority Data

Jan. 6, 1970 Switzerland............................ 103/70

[52] U.S. Cl................................ 260/289 R; 424/258
[51] Int. Cl.²........................................ C07D 217/24
[58] Field of Search ................................ 260/289 R

[56] References Cited
UNITED STATES PATENTS

| | | | |
|---|---|---|---|
| 3,393,198 | 7/1968 | Unger............................ | 260/289 R |
| 3,577,424 | 5/1971 | Ehrhart et al.................. | 260/288 R |
| 3,666,763 | 5/1972 | Grethe............................ | 260/289 R |
| 3,745,162 | 7/1973 | Helsley........................... | 260/289 R |

OTHER PUBLICATIONS

Hinton et al., Chem. Abstr., Vol. 53 Col. 15082–15085 (1959).
Rheiner, Chem. Abstr., Vol. 75 Col. 129683c (1971) Abstracting German 2,062,001.
Burger, "Medicinal Chemistry", 2d ed. Interscience, 1960, p. 43.

*Primary Examiner*—Richard J. Gallagher
*Assistant Examiner*—James H. Turnipseed
*Attorney, Agent, or Firm*—Samuel L. Welt; Bernard S. Leon; Frank P. Hoffman

[57] ABSTRACT

4-Phenyl isoquinolines wherein the 4-phenyl ring is substituted with a halogen or nitro group and processes for their preparation are described. The end products are useful as antidepressant agents.

14 Claims, No Drawings

SUBSTITUTED 4-PHENYL ISOQUINOLINES

RELATED APPLICATIONS

The present application is a divisional application of copending application Ser. No. 102,551 filed Dec. 29, 1970, now abandoned in the name of Dr. Rheiner.

DESCRIPTION OF THE INVENTION

This invention relates to novel 1,2,3,4-tetrahydro-4-phenyl-isoquinolines and processes of making the foregoing.

The novel 1,2,3,4-tetrahydro-4-phenyl-isoquinolines to which the invention relates are selected from the group consisting of compounds of the formula

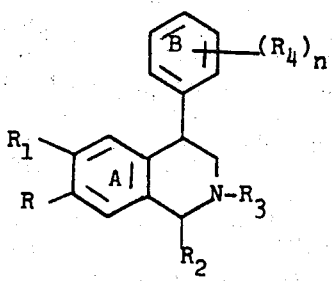

I wherein R signifies hydroxy or lower alkoxy, $R_1$ signifies hydrogen, hydroxy or lower alkoxy, or R and $R_1$ taken together signify methylenedioxy; $R_2$ signifies hydrogen or lower alkyl; $R_3$ signifies lower alkyl or aryl-lower alkyl; $R_4$ signifies halogen, nitro, mono-lower alkylamino, di-lower alkylamino or amino and n is an integer from 1 to 2
and the pharmaceutically acceptable acid addition salts thereof.

As used herein, the term "lower alkyl" denotes a hydrocarbon group containing from 1 to 4 carbon atoms such as, for example, methyl, ethyl, propyl, isopropyl, butyl and the like, with methyl being preferred. The term "lower alkoxy" denotes a lower alkyl-ether group in which the lower alkyl moiety is as described above such as methoxy, ethoxy, propoxy and the like, with methoxy being preferred. As used herein the term "halogen" denotes all four forms thereof, i.e. fluorine, chlorine, bromine and iodine unless specified otherwise. The expression "acyl" denotes the residue of an organic acid obtained by removal of a hydroxy group; the preferred acyl groups are lower alkanoyl groups. The term "aryl-lower alkyl" denotes straight-chain or branched-chain saturated hydrocarbon residues with 1–4 carbon atoms which are substituted by a phenyl residue, such as, for example, benzyl, 2-phenylethyl and the like. The term "lower alkanoyl" denotes the residue of an aliphatic saturated carboxylic acid with at most 4 carbon atoms such as acetyl, propionyl and the like.

Preferred among the compounds of formula I are those wherein the $R_1$ substituent is hydrogen, that is, those compounds wherein the A-phenyl ring is mono-substituted. Further preferred are those compounds wherein $R_1$ is hydrogen and R is a methoxy group.

A further preferred group of compounds falling within the scope of formula I are those in which the two ortho positions of the B-phenyl ring are unsubstituted; that is, those compounds which display a substituent or substituents denoted as $R_4$ in the para and/or in the meta positions of said phenyl ring. This preferred group of compounds may be characterized by the following formula:

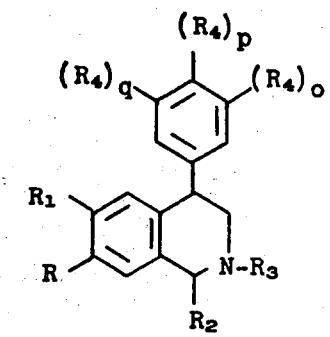

Ia wherein R, $R_1$, $R_2$, $R_3$ and $R_4$ are as described above, o, p and q are the integers 0 or 1, and one or two of the characters o, p or q is the integer 0.
and the pharmaceutically acceptable acid addition salts of these compounds.

A particularly preferred group of compounds are those falling within the scope of formula Ia wherein $R_4$ signifies halogen, preferably chlorine, p is the integer 1 and q is the integer 0, i.e. compounds of the formula

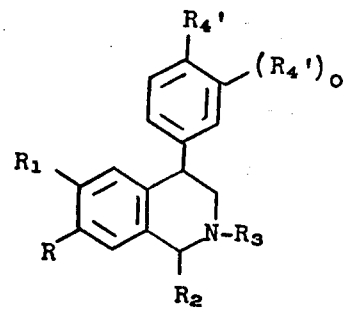

Ib wherein R, $R_1$, $R_2$, $R_3$ and o are as described above and $R_4{'}$ signifies halogen, preferably chlorine, and the pharmaceutically acceptable acid addition salts thereof.

A further preferred group of compounds within the scope of the present invention are the compounds of formula I wherein the $R_3$ substituent in the 2-position of the isoquinoline molecule is a methyl or an ethyl group. Likewise, the compounds of formula I wherein the $R_2$ substituent in the 1-position of the isoquinoline molecule is hydrogen are preferred.

The most preferred of the compounds of the present invention falling within the scope of formula I are:
  4-(4-chlorophenyl)-1,2,3,4-tetrahydro-7-hydroxy-2-methylisoquinoline;
  4-(3,4-dichlorophenyl)-1,2,3,4-tetrahydro-7-hydroxy-2-methylisoquinoline;
  4-(3,4-dichlorophenyl)-1,2,3,4-tetrahydro-7-methoxy-2-methylisoquinoline;
  4-(4-chlorophenyl)-1,2,3,4-tetrahydro-7-methoxy-2-methylisoquinoline.

The compounds of formula I above are basic in nature and may be obtained in the form of their acid addition salts. In a most preferred embodiment these salts are formed with pharmaceutically acceptable acid groups. These salts may be prepared from the free base form of the 1,2,3,4-tetrahydro-4-phenylisoquinolines by methods well known in the art. Examples of such pharmaceutically acceptable acid groups include those of inorganic and organic acids such as hydrochloric acid, hydrobromic acid, sulfuric acid, acetic acid, succinic acid, maleic acid, methane-, benzene- or para-toluene sulfonic acid and the like. In addition, non-pharmaceutically acceptable acid salts of the above 4-phenylisoquinoline compounds are useful as intermediates in the preparation of pharmaceutically acceptable acid addition salts of said compounds by salt exchange methods or by conversion of the non-acceptable salt to the free base followed by formation of the salt using the pharmaceutically acceptable acid. Both such methods of converting the pharmaceutically non-acceptable salt to pharmaceutically acceptable form utilize procedures well known in the art.

The compounds of formula I above may be prepared following a variety of synthetic routes.

A. In one process aspect of the present invention, the compounds of formula I above and their acid addition salts may be prepared by cyclizing a compound of the formula

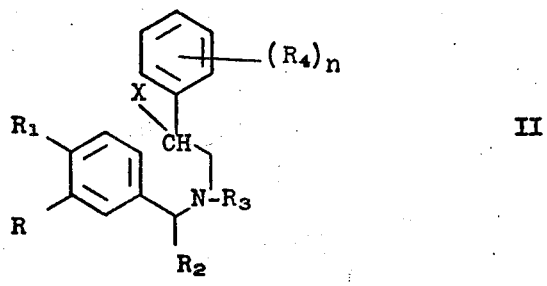

wherein R, $R_1$–$R_4$ and $n$ are as described above and X signifies hydroxy, acyloxy or a halogen atom.

The cyclization of a compound of formula II above to form the desired compounds of formula I is effected in the presence of an acidic cyclization agent. Suitable acidic cyclization agents for the purposes of this process aspect include hydrochloric acid, sulfuric acid, phosphoric acid, polyphosphoric acid, boron trifluoride, aluminum chloride, tin tetrachloride and the like. The choice of the acidic cyclization agent utilized depends upon the nature of the X substituent in the compounds of formula II. It should be noted that, depending upon the reaction conditions employed, any lower alkoxy groups present as the R and/or $R_1$ substituent can be converted by ether-cleavage into hydroxy groups or can be retained as alkoxy groups. The cyclization of a compound of formula II can also be effected in the presence of an inert organic solvent. Although temperature and pressure are not critical to the successful performance of this process aspect, this reaction is expediently effected using temperatures in a range of from about 10° to about 150°.

B. In a further process aspect of the present invention, the novel compounds of formula I wherein $R_4$ signifies halogen, nitro or di-lower alkylamino may be prepared by alkylating a compound of the general formula

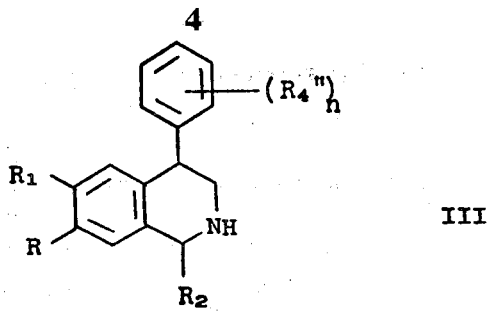

wherein R, $R_1$, $R_2$ and $n$ are as described above and $R_4''$ signifies halogen, nitro or di-lower alkylamino.

The alkylation of the compound of formula III above which effects introduction of a lower alkyl group or an aryl-lower alkyl group into the 2-position of the isoquinoline molecule may be effected following conventional alkylation techniques, for example by reacting the starting materials of formula III with an alkylating agent. Examples of suitable alkylating agents for this purpose include lower alkyl or aryl-lower alkyl halides, such as methyl iodide, ethyl iodide, methyl bromide, benzyl bromide and the like; suitable sulfates such as dimethyl sulfate; or sulfonic acid methyl ester, para-toluene sulfonic acid benzyl ester and the like.

Alternatively, it is also possible to introduce the lower alkyl or aryl-lower alkyl group into the 2-position by first introducing a formyl, alkanoyl, benzoyl or phenylalkanoyl group into the 2-position of the isoquinoline molecule, for example, by means of reacting the compound of formula III with acetic anhydride, acetyl chloride, benzoylchloride and the like reagents. The end product obtained from this reaction is then reduced by means of lithium aluminum hydride treatment to yield the corresponding compound bearing a lower alkyl or aryl-lower alkyl substituent in the 2-position. In another alternative procedure, a methyl group can be introduced into the 2-position of the isoquinoline molecule by treating the compound of formula III above with formaldehyde in formic acid or with formaldehyde and subsequently with catalytically activated hydrogen. The choice of the alkylation procedure to be employed is obviously governed by the nature of the lower alkyl or aryl-lower alkyl substituent to be introduced and by the nature of the various other substituents found in the starting material of formula III. Thus, for example, the reaction conditions can be varied following known procedures in order to effect or to avoid alkylation of any hydroxy substituent found in the 6- or 7-positions, while at the same time effecting introduction of the lower alkyl or aryl-lower alkyl substituent into the 2-position.

C. In still another process aspect of the present invention, the compounds of formula I wherein $R_4$ signifies halogen or di-lower alkylamino, R and $R_1$ are other than hydroxy and $R_3$ is other than benzyl may be prepared by reducing under acidic conditions a compound of the general formula

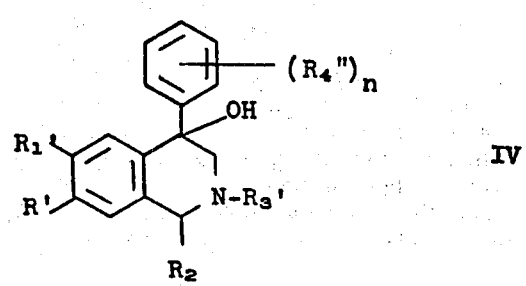

wherein R' signifies lower alkoxy, $R_1'$ signifies hydrogen or lower alkoxy or R' and $R_1'$ taken together signify methylenedioxy, $R_3'$ signifies lower alkyl or aryl-lower alkyl other than benzyl, $R_4''$ signifies halogen or di-lower alkylamino, and $R_2$ and $n$ are as described above.

The reduction of the compounds of formula IV above is effected under acidic conditions. For example, reduction may be effected in the presence of glacial acetic acid, hydrochloric acid of various concentrations, alcoholic hydrogen chloride and the like. Catalytically activated hydrogen is used as the reducing agent. Suitable catalysts for this purpose include platinum oxide, mixtures of platinum oxide and platinum black, rodium on charcoal or on aluminum oxide, and palladium on charcoal, with palladium on charcoal being the preferred catalyst. Under the acidic conditions employed for this reduction dehydration of the formula IV compound may occur resulting in the formation of the dihydroisoquinoline intermediate of formula V.

D. In a further process aspect of the present invention, compounds of formula I above wherein $R_4$ signifies halogen or di-lower alkylamino, R and $R_1$ are other than hydroxy and $R_3$ is other than benzyl may be prepared by the reduction of a compound of the formula

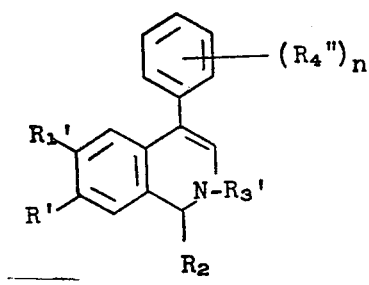

V wherein R', $R_1'$, $R_2$, $R_3'$, $R_4''$ and $n$ are as described above.

The reduction of compounds of formula V above to yield the desired compounds of formula I is accomplished utilizing catalytically activated hydrogen. Under acidic conditions compounds of formula V easily disproportionate to compounds of formula I and isoquinolinium salt intermediates, which are not separated. These intermediates can be reduced with complex metal hydrides such as alkali metal hydrides, preferably sodium borohydride, or with catalytically activated hydrogen. Suitable catalysts for this purpose are the same as discussed for process aspect C.

E. In a further process aspect of the present invention, compounds of formula I wherein $R_4$ signifies halogen or di-lower alkyl-amino and $R_1$ is other than hydrogen may be prepared by reducing a quaternary compound of the formula

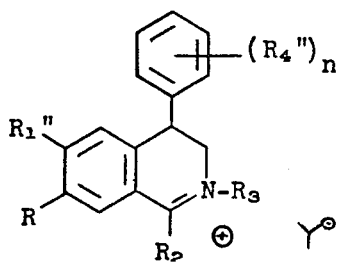

VI wherein $R_1''$ is hydroxy or lower alkoxy, or $R_1''$ and R together are methylenedioxy, R, $R_2$, $R_3$, $R_4''$ and $n$ are as described above and Y is an acid anion.

The compounds of formula VI above may be converted to the corresponding compounds of formula I by treatment with a suitable reducing agent. Examples of such suitable reducing agents include nascent or catalytically activated hydrogen and complex alkali metal hydrides, such as sodium borohydride or lithium aluminum hydride, and the like. If catalytically activated hydrogen is used as the reducing agent, suitable catalysts include platinum oxide, mixtures of platinum oxide and platinum black, rodium on charcoal or on aluminum oxide and palladium on charcoal, with palladium on charcoal being the preferred catalyst. The choice of the specific reducing agent employed is influenced by and depends upon the nature of the substituents present in the starting material of formula VI. Thus, where $R_3$ in the starting material represents a benzyl group and it is desired to retain such group in the end product, sodium borohydride should be used at the reducing agent.

In effecting the reductions described in process aspects D and E above, the reaction is expediently effected in the presence of an inert organic solvent. Suitable solvents for this purpose include alcohols, such as methanol, ethanol and the like.

F. In a further process aspect of the present invention, compounds of formula I wherein $R_4$ signifies halogen, amino, mono-lower alkyl-amino or di-lower alkylamino and $R_3$ is other than benzyl may be prepared by reducing a compound of the formula

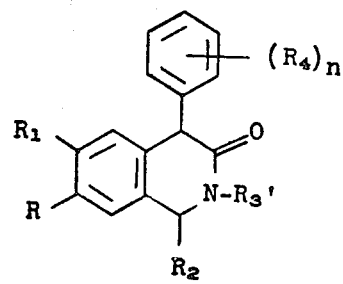

VII wherein R, $R_1$, $R_2$, $R_3'$, $R_4$ and $n$ are as described above.

The reduction of the compounds of formula VII above to the desired corresponding compounds of formula I is accomplished by employing lithium aluminum hydride as the reducing agent. The reaction is effected in the presence of any inert organic solvent conventionally used in lithium aluminum hydride reductions. Examples of suitable inert organic solvents include open chain or cyclic ethers such as diethyl ether, tetrahydrofuran, dioxane and the like. It will be appreciated that in this reduction any nitro group as the $R_4$ substituent will not be retained but will be converted into an amino group.

G. In a further process aspect of the present invention, compounds of formula I wherein R and/or $R_1$ signifies a hydroxy group may be prepared by subjecting the corresponding compound of formula I wherein R and/or $R_1$ signify a lower alkoxy group to an acidic ether cleavage. The ether cleavage may be carried out employing conventional techniques as for example by heating the compound in about a 48 percent hydrogen bromide solution. A suitable temperature range for this reaction is from about 80° C to the boiling point of the reaction mixture, with a temperature of about 125° C being preferred.

H. In a further process aspect, compounds of formula I wherein $R_4$ signifies an amino group and $R_3$ is other than benzyl may be prepared by reducing corresponding compounds of formula I wherein $R_4$ signifies nitro. The reduction of the nitro group at $R_4$ to the amino group may be accomplished following conventional techniques, for example by employing a reducing agent such as nascent or catalytically activated hydrogen, lithium aluminum hydride and the like. If catalytically activated hydrogen is employed as the reducing agent, the catalysts that can be employed are the same as those discussed in process aspect C above.

I. In a further process aspect, the compounds of formula I wherein $R_4$ represents mono-lower alkylamino or di-lower alkylamino may be prepared by monoalkylating the corresponding formula I compound wherein $R_4$ signifies amino or mono-lower alkylamino. This mono-alkylation is carried out according to generally known methods. The choice of the alkylation procedure to be employed is governed primarily by the nature of the other substituents on the molecule. Thus, for example, it is possible to so choose the alkylation conditions so that any hydroxy groups present are not attacked.

J. In a further process aspect, the compounds of formula I wherein at least one of R and $R_1$ represents hydroxy, $R_3$ is other than benzyl and $R_4$ is other than nitro may be prepared by hydrolytically debenzylating the corresponding compound of formula I wherein at least one of R and $R_1$ represents a benzyloxy group. This catalytic debenzylation can be accomplished following conventional techniques.

A number of compounds embraced by formula I above are optically active since the carbon atom in the 4-position of the isoquinoline molecule is a center of asymmetry. These optically active 1,2,3,4-tetrahydro-4-phenylisoquinolines may be prepared by the resolution of the racemic mixture. This resolution of the racemate into the optically active antipodes is effected following conventional techniques, for example, by reaction of the racemate with a suitable optically active acid, followed by the separation of the two diastereomeric salts obtained, for example by fractional crystallization and subsequent freeing of the optically uniform base. Suitable optically active acids for this purpose include (-)di-O-isopropylidene-2-keto-L-gulonic aicd hydrate (DAG) and O,O-dibenzoyl -d-or-l-tartaric acid (d or L - DBT). Compounds of formula I which display more than one center of asymmetry, for instance those compounds wherein $R_2$ is other than hydrogen, can occur in different diastereomeric forms. Mixtures of such diastereomers can be separated by separation techniques which are generally known in the art. By such methods, these mixtures can be separated into the individual racemic mixtures, which can, in turn, be split into their optically active components as discussed above.

A further possibility of the manufacture of an optically uniform compound of formula I consists in using an optically uniform starting material. It is preferred to use an optically uniform starting material of formula III as such can be separated in accordance with usual procedures.

The compounds employed as starting materials in the processes discussed above can be obtained following known procedures. Representative examples for the preparation of such starting materials are presented in the following reaction schemes. Obviously these synthetic routes must be appropriately modified for the preparation of differently substituted compounds.

REACTION SCHEME A

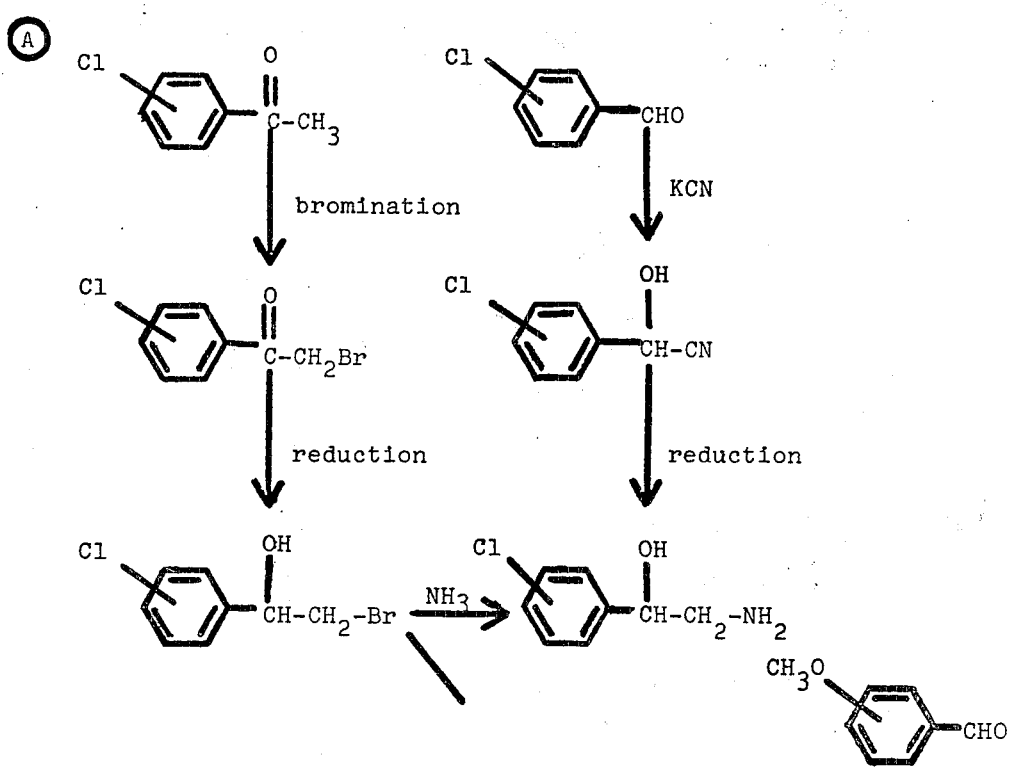

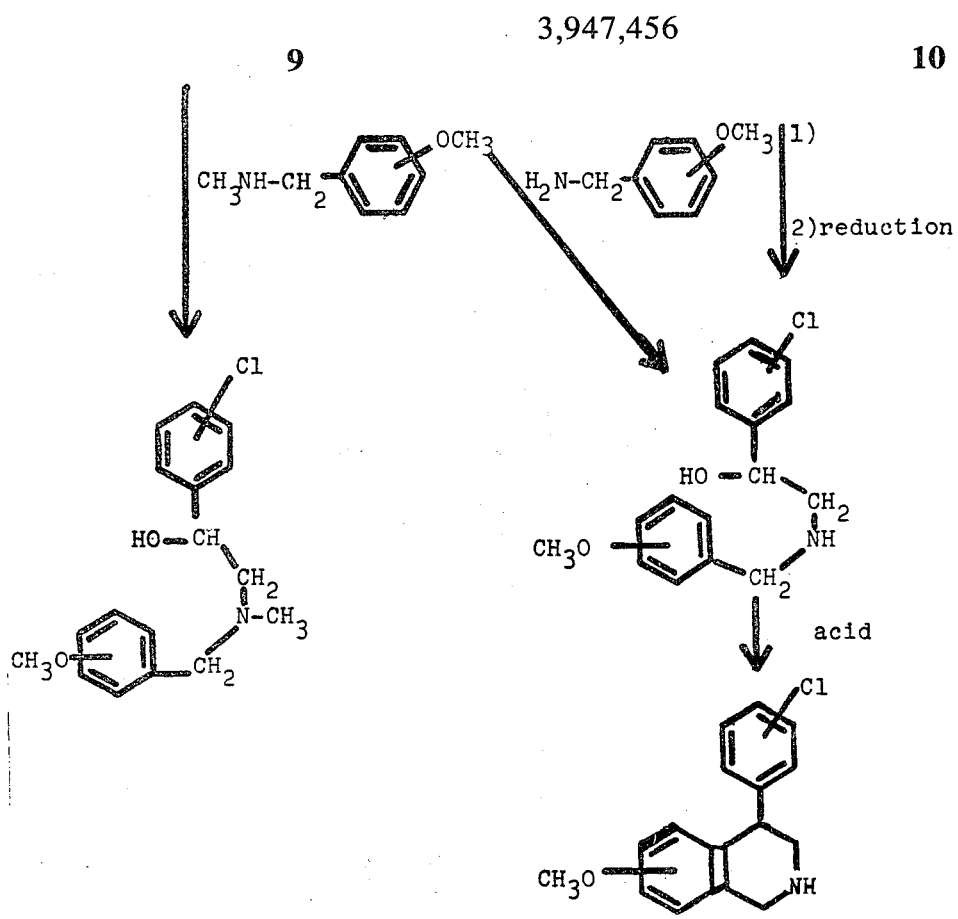
REACTION SCHEME B
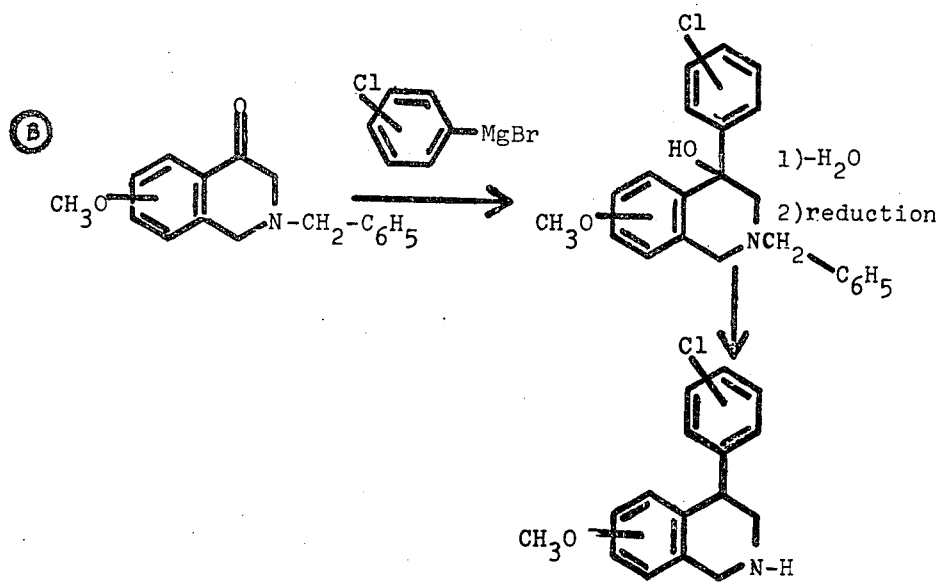
REACTION SCHEME C
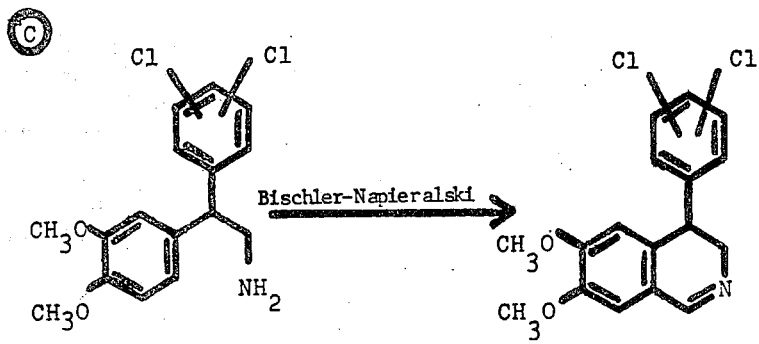

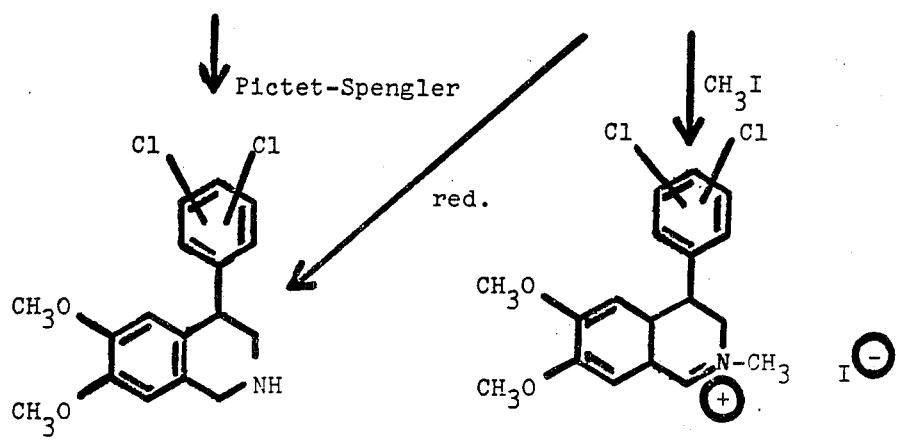

REACTION SCHEME D

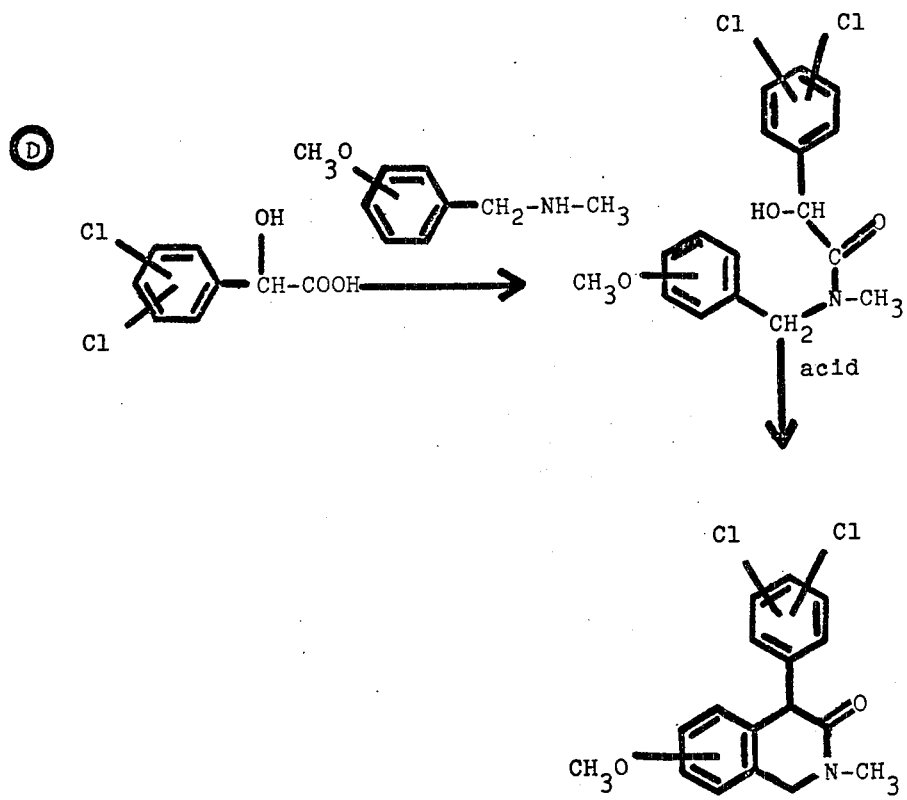

The compounds of formula I above and their pharmaceutically acceptable salts are extremely effective and active as anti-depressant agents. Their useful anti-depressant activity is shown in warm-blooded animals utilizing standard test procedures. Thus to demonstrate this anti-depressant activity, the preparation to be tested was applied in three doses each of 50 mg/kg p.o. (twice on the day before, once on the day of the experiment) to groups of 5 rats each. Six hours after the last administration the animals received 20 mg/kg of 2-ethyl-2-hydroxy-3-isobutyl-9,10-dimethoxy-1,3,4,6,7,11b-hexahydro-2H-benzo (a) quinolizine hydrochloride injected subcutaneously. The same dosage was administered to a group of 5-non-pretreated rats. The evaluation includes central and peripheral symptoms such as are characteristic for anti-depressants (See *Annals of the New York Academy of Science*, Vol. 96, page 279, 1962). Especially observed were the motility (climbing), sensitivity to stimulus, seeking behavior as well as the suppression of ptosis. These changes were expressed in numbers according to an evaluation scheme.

Following the test procedures described above, the compounds set out in Table I hereinafter displayed a strong anti-depressant action which manifested itself in strongly increased, characteristic motility, sensitivity to stimulus, seeking behavior as well as complete suppression of ptosis. The percentage numbers stated relate to the value obtained with amitriptyline (amitriptyline = 100 percent).

The low toxicity of the compounds of formula I is also illustrated by the acute toxicity ($LD_{50}$) of the compounds set out in Table I. The figures set forth in Table I as to acute toxicity refer to toxicity tests performed in mice and are the 24 hour values.

Table 1

| Compound | Activity in % of the activity of amitriptyline | $LD_{50}$ in mg/kg | | |
|---|---|---|---|---|
| | | i.v. | s.c. | p.o. |
| 4-(3,4-dichlorophenyl)-1,2,3,4-tetrahydro-7-methoxy-2-methylisoquinoline | about 128 | 125–250 | 500–1000 | 1000–2000 |
| 4-(3,4-dichlorophenyl)-1,2,3,4-tetrahydro-2-methyl-7-isoquinolinol | about 158 | 30–60 | 250–500 | 500–1000 |
| 4-(4-chlorophenyl)-1,2,3,4-tetrahydro-2-methyl-7-isoquinolinol | about 114 | 30–60 | 500–1000 | 1000–2000 |

The compounds of formula I can be used in the form of conventional pharmaceutical preparations. For example, said compounds or their pharmaceutically acceptable salts can be mixed with a pharmaceutical, organic or inorganic inert carrier material which is suitable for enteral (e.g. oral) or parenteral application — such as, for example, water, gelatin, lactose, starches, magnesium stearate, talc, vegetable oils, gum arabic, polyalkylene glycols, Vaseline, etc. The pharmaceutical preparations can be submitted in solid form (e.g. as tablets, dragees, suppositories, capsules) or in liquid form (e.g. as solutions, suspensions or emulsions). They may be sterilized and/or contain additives such as preserving, stabilizing, wetting or emulsifying agents, salts for varying the osmotic preessure or buffers. They can also contain yet other therapeutically valuable substances.

Expedient pharmaceutical dosage forms contain about 1 to 200 mg of a compound of formula I. Expedient oral dosage ranges for mammals lie at about 0.1 mg/kg per day to about 5 mg/kg per day. Expedient parenteral dosage ranges for mammals lie at about 0.1 mg/kg per day to about 1.0 mg/kg per day. However, the ranges mentioned can be extended upwards or downwards according to individual requirement and directions of the specialist.

The following examples further illustrate the invention. All temperatures are in degrees centigrade unless otherwise mentioned.

EXAMPLE 1

The free base isolated from 1.55 g. of rac.-4-(4-chlorophenyl)-1,2,3,4-tetrahydro-7-methoxyisoquinoline hydrochloride is shaken with 1.1 ml. of a 35% formaldehyde solution and the mixture is allowed to stand at room temperature for 2 hours. It is hydrogenated over 1 g. of Raney nickel, filtered from the catalyst, the filtrate is evaporated and the residue is crystalized with ethanolic hydrogen chloride, methanol and ether. Recrystallization from methanol-ether gives rac.-4-(4-chlorophenyl)-1,2,3,4-tetrahydro-7-methoxy-2-methylisoquinoline hydrochloride, m.p. 244°–146°.

The starting material can, for example, be manufactured as follows:

4-Chlorobenzaldehyde is converted into the cyanohydrin and this is reduced by means of lithium aluminum hydride to rac.-α-(aminomethyl)-4-chlorobenzyl alcohol.

The free base is prepared from 41.6 g. of rac.-α-(aminomethyl)-4-chlorobenzyl alcohol hydrochloride, and taken up in 400 ml. of benzene, 30 g. of 3-methoxybenzaldehyde are added and the mixture is heated at reflux using a water-separator until all water has been removed. The mixture is thereupon evaporated, the residue is dissolved in 400 ml. of methanol, 15 g. of sodium borohydride are added in small portions with ice-cooling and the mixture is stirred at room temperature for 6 hours. Evaporation, solvent extraction crystallization with ethanolic hydrogen chloride, methanol and ether and recrystallization from methanol-ether gives 49.5 g. of rac.-4-chloro-α-{[(3-methoxybenzyl)amino]methyl}benzyl alcohol hydrochloride, m.p. 198°–199°. After recrystallization from ether-petroleum ether the free base displays a m.p. of 88°–90°.

91.0 G. of rac.-4-chloro-α-{[(3-methoxybenzyl)amino]methyl}benzyl alcohol hydrochloride are stirred under argon for one hour at 100° with 1450 ml. of a mixture of 1 part by volume of sulfuric acid (d = 1.84) and 1 part by volume of water. After cooling, the mixture is poured onto about 10 kg. of ice and 1.1 kg. of sodium hydroxide and extracted with methylene chloride. The extracts, washed with saturated sodium chloride solution, yield, after drying and evaporation, about 78 g. of a dark-yellow oil.

Chromatography of this oil on 7 kg. of silica gel yields 2 main fractions. After treatment with ethanolic hydrogen chloride, crystallization with ethyl acetate and ether and recrystallization from methanol-ether, the first fraction yields 22.0 g. of rac.-4-(4-chlorophenyl)-1,2,3,4-tetrahydro-5-methoxyisoquinoline hydrochloride, m.p. 236°–238°. The second fraction yields, after analogous treatment, 43.6 g. of rac.-4-(4-chlorophenyl)-1,2,3,4-tetrahydro-7-methoxyisoquinoline hydrochloride, m.p. 200°–202°.

EXAMPLE 2

The free base prepared from 12.2 g. of rac.-4-(4-chlorophenyl)-1,2,3,4-tetrahydro-7-methoxy-2-methylisoquinoline hydrochloride is stirred at reflux with 150 ml. of 48% hydrobromic acid solution for 2 hours at a bath temperature of 160°. After evaporation and recrystallization from methanol-ether there is obtained rac.-4-(4-chlorophenyl)-1,2,3,4-tetrahydro-2-methyl-7-isoquinolinol hydrobromide of m.p. 292°–293°. The free base of this compound displays a m.p. of 189°–190° after recrystallization from ether, the hydrochloride after recrystallization from methanol-ether melts at 295°–297°.

EXAMPLE 3

The free base isolated from 8.0 g. of rac.-4-(3-chlorophenyl)-1,2,3,4-tetrahydro-7-methoxyisoquinoline hydrochloride is taken up in 150 ml. of methanol, 6 ml. of a 35% formaldehyde solution are added and the mixture is shaken until the precipitate formed again completely dissolves. The mixture is thereupon hydrogenated over 6 g. of Raney nickel, filtered and, after acidification with ethanolic hydrogen chloride, crystallized. Recrystallization from methanol-ether gives rac.-4-(3-chlorophenyl)-1,2,3,4-tetrahydro-7-methoxy-2-methylisoquinoline hydrochloride, m.p. 250°–251°.

The starting material can be manufactured as follows:

3-Chlorobenzaldehyde is converted into the cyanohydrin and this is reduced by means of lithium aluminum hydride to rac.-α-(aminomethyl)-3-chlorobenzyl alcohol.

The free base is prepared from 18.5 g. of rac.-α-(aminomethyl)-3-chlorobenzyl alcohol hydrochloride and is taken up in 200 ml. of benzene, 13.4 g. of 3-methoxybenzaldehyde are added and the mixture is heated at reflux using a water-separator until all water has been removed. It is thereupon evaporated, the residue is dissolved in 300 ml. of methanol, 8 g. of sodium borohydride are added with ice-cooling, the mixture is allowed to stand for 18 hours and it is then evaporated. After solvent extraction acidification with ethanolic hydrogen chloride and recrystallization from methanol-ether, there are obtained 23.2 g. of rac.-3-chloro-α-{[(3-methoxybenzyl)amino]methyl}benzyl alcohol hydrochloride, m.p. 174°–175°. After recrystallization from ether-petroleum ether, the free base displays a m.p. of 98°–100°.

30.0 G. of rac.-3-chloro-α-{[(3-methoxybenzyl)amino]methyl}benzyl alcohol hydrochloride are stirred for 2 hours at 100° in a mixture of equal parts of concentrated sulfuric acid and water. The cooled solution is poured onto a mixture of ice and sodium hydroxide (excess of alkali) and extracted with methylene chloride. By chromatography on silica gel, two uniform substances are separated from each other which crystallize after acidification with ethanolic hydrogen chloride and treatment with ether. Recrystallization of the first substance from methanol-ether gives 7.2 g. of rac.-4-(3-chlorophenyl)-1,2,3,4-tetrahydro-5-methoxyisoquinoline hydrochloride, m.p. 230°–232°. The base manufactured therefrom displays a m.p. of 93°–95° after recrystallization from ether-petroleum ether. After analogous working up, the other substance yields 14.1 g. of rac.-4-(3-chlorophenyl)-1,2,3,4-tetrahydro-7-methoxyisoquinoline hydrochloride, m.p. 217°–219°.

EXAMPLE 4

The free base isolated from 4.00 g. of rac.-4-(3-chlorophenyl)-1,2,3,4-tetrahydro-7-methoxy-2-methylisoquinoline hydrochloride is heated for an hour at 150° (bath temperature) with 80 ml. of 48% hydrobromic acid. After concentration, it is extracted with ethyl acetate and sodium bicarbonate solution. By acidification of the ethyl acetate extract with ethanolic hydrogen chloride and by crystallization and recrystallization from methanol-ether there is obtained rac.-4-(3-chlorophenyl)-1,2,3,4-tetrahydro-2-methyl-7-isoquinolinol hydrochloride, m.p. 258°–259°. The base released therefrom displays a m.p. of 196°–197° after recrystallization from ether-petroleum ether.

EXAMPLE 5

The free base prepared from 19 g. of rac.-4-(4-chlorophenyl)-1,2,3,4-tetrahydro-6,7-dimethoxyisoquinoline hydrochloride is taken up with 300 ml. of methanol and 15 ml. of 35% formalin solution and allowed to stand at room temperature for 2 hours. After hydrogenation over Raney nickel, treatment with ethanolic hydrogen chloride and recrystallization from methanol-ether, there are obtained 18.7 g. of rac.-4-(4-chlorophenyl)-1,2,3,4-tetrahydro-6,7-dimethoxy-2-methylisoquinoline hydrochloride, m.p. 190°–220°. The free base crystallizes from ether-petroleum ether, m.p. 101°–102°.

The starting material can be manufactured as follows:

4-Chlorobenzaldehyde is converted into the cyanohydrin and this is reduced with lithium aluminum hydride to rac.-α-(aminomethyl)-4-chlorobenzyl alcohol.

The free base prepared from 6.0 g. of rac.-α-(aminomethyl)-4-chlorobenzyl alcohol hydrochloride is taken up in 200 ml of benzene and boiled at reflux with 5.3 g. of veratraldehyde for one hour using a water separator. The residue obtained after concentration is taken up in 200 ml. of methanol and reduced at 5° with 2.5 g. of sodium borohydride. After evaporation, solvent extraction, acidification with ethanolic hydrogen chloride and recrystallization from methanol-ether, there are obtained 9.6 g. of rac.-4-chloro-α-{[(3,4-dimethoxybenzyl)amino]methyl}benzyl alcohol hydrochloride, m.p. 220°–221°. The free base displays a m.p. of 93°–94° after recrystallization from etherpetroleum ether.

At room temperature with stirring, 7.12 g. of rac.-4-chloro-α-{[(3,4-dimethoxybenzyl)amino]methyl}benzyl alcohol hydrochloride are introduced into 100 ml. of a mixture of equal parts by volume of conc. sulfuric acid and water and heated of 80° for 30 minutes. After rendering alkaline, extraction of the base with methylene chloride, acidification with ethanolic hydrogen chloride and recrystallization from ethanol-ether there is obtained rac.-4-(4-chlorphenyl)-1,2,3,4-tetrahydro-6,7-dimethoxyisoquinoline hydrochloride of m.p. 186°–187°. The free base displays a m.p. of 118°–119° after recrystallization from ether.

EXAMPLE 6

The free base isolated from 1.80 g. of rac.-4-(4-chlorophenyl)-1,2,3,4-tetrahydro-6,7-dimethoxy-2-methylisoquinoline hydrochloride is stirred for 3 hours with 30 ml. of 48% hydrogen bromide solution at 150° (bath temperature). After concentration and recrystallization from methanol-ether, there is obtained rac.-4-(4-chlorophenyl)-1,2,3,4-tetrahydro-2-methyl-6,7-isoquinolinediol hydrobromide, m.p. 280°–281°.

EXAMPLE 7

The free base prepared from 5.20 g. of rac.-4-(3,4-dichlorophenyl)-1,2,3,4-tetrahydro-7-methoxyisoquinoline hydrochloride is stirred at room temperature with 75 ml. of methanol and 3.8 ml. of 35% formaldehyde solution for 2 hours and thereupon hydrogenated over 2 g. of Raney nickel. After filtering off, evaporation, acidification with ethanolic hydrogen chloride, crystallization and recrystallization from methanol-ether, there is obtained rac.-4-(3,4-dichlorophenyl)-1,2,3,4-tetrahydro-7-methoxy-2-methylisoquinoline hydrochloride, m.p. 273°–275°.

The starting material can be manufactured as follows:

3,4-Dichlorobenzaldehyde is converted into the cyanohydrin and this is reduced with lithium aluminum hydride, or α-chloro-3,4-dichloroacetophenone is reduced with sodium borohydride and the chlorohydrin obtained is reacted with ammonia, rac.-α-(aminomethyl)-3,4-dichlorobenzyl alcohol being obtained in both cases.

The free base obtained from 70.0 g. of rac.-α-(aminomethyl)-3,4-dichlorobenzyl alcohol hydrochloride is heated at reflux in 1 l. of benzene with 40.8 g. of 3-methoxybenzaldehyde using a water-separator for 2 hours until no more water is released. After concentration and dissolving in 1 l. of methanol, the product is reduced with 30 g. of sodium borohydride below 5°, evaporated and extracted with methylene chloride and water. The methylene chloride extract, acidified with ethanolic hydrogen chloride, crystallizes with ethyl acetate and, after recrystallization from methanol-ether, yields rac.-3,4-dichloro-α-{[(3-methoxybenzyl)amino]methyl}benzyl alcohol hydrochloride, m.p. 198°–200°. The free base recrystallized from methanol-petroleum ether has a m.p. of 94°–95°.

100 G. of rac.-3,4-dichloro-α-{[(3-methoxybenzyl)amino]-methyl}benzyl alcohol hydrochloride are introduced with stirring into 1 l. of a mixture of 1 part by volume of sulfuric acid (d = 1.84) and 1 part by volume of water and heated for 8 hours in a bath of 100°. After cooling, the mixture is poured into a cooled solution of 1 kg. of sodium hydroxide in ice-water and extracted with methylene chloride. Chromatography of the extract (80 g. of crude product) on 4 kg. of silica gel yields two main fractions which are uniform according to thin layer chromatography. Acidification with ethanolic HCl, crystallization with ethyl acetate and recrystallization from methanol-ether gave 19.8 g. of rac.-4-(3,4-dichlorophenyl)-1,2,3,4-tetrahydro-5-methoxyisoquinoline hydrochloride, m.p. 255°–256° and 45.1 g. of rac.-4-(3,4-dichlorophenyl)-1,2,3,4-tetrahydro-7-methoxyisoquinoline hydrochloride, m.p. 243°–244°.

EXAMPLE 8

The free base obtained from 2.00 g of rac.-4-(3,4-dichlorophenyl)-1,2,3,4-tetrahydro-7-methoxy-2-methylisoquinoline hydrochloride is heated at reflux for one hour with 48% hydrogen bromide solution at a bath temperature of 160°. After evaporation and recrystallization from methanol-ether, there are obtained 2.0 g of rac.-4-(3,4-dichlorophenyl)-1,2,3,4-tetrahydro-2-methyl-7-isoquinolinol hydrobromide, m.p. 284°–285°. The free base recrystallized from ether-petroleum ether has the m.p. 212°–215.5°; the hydrochloride after recrystallization from methanol-ether melts at 287°–288° (decomposition, softening at 280°).

EXAMPLE 9

The free base obtained from 11.6 g of rac.-1,2,3,4-tetrahydro-7-methoxy-4-(4-nitrophenyl)-isoquinoline hydrochloride is heated at reflux for one hour with 14 ml of formic acid and 14 ml of 35% formaldehyde solution. After evaporation in vacuum, extraction between methylene chloride and sodium bicarbonate solution, treatment of the organic phase with ethanolic hydrogen chloride and recrystallization from methanol-ether, there are obtained 10.2 g. of almost white rac.-1,2,3,4-tetrahydro-7-methoxy-2-methyl-4-(4-nitrophenyl)-isoquinoline hydrochloride, m.p. 250°–251° (dec.).

The starting material can be manufactured as follows:

4-Nitroacetophenone is brominated in the α-position, the product obtained is redcuced by means of sodium borohydride to the corresponding bromohydrin and this is treated with ammonia. Rac.-α-(aminomethyl)-4-nitrobenzyl alcohol, m.p. 138°–139° (from ethyl acetate) is obtained.

4 G. of rac.-α-(aminomethyl)-4-nitrobenzyl alcohol are boiled at reflux in 50 ml. of benzene with 3.4 g. of 3-methoxybenzaldehyde using a water-separator until no more water comes out. After evaporation, the product is reduced in 200 ml. of methanol with ice-cooling with a total of 2g. of sodium borohydride and stirred at room temperature for 1 hour. After concentration, extraction with methylene chloride and water, acidification with ethanolic hydrogen chloride and recrystallization from methanol-ether, there are obtained 6.9 g. of rac.-α-{[(3-methoxybenzyl)amino]methyl}-4-nitrobenzyl alcohol hydrochloride, m.p. 248°–249°. The free base displays a m.p. of 117°–119° after recrystallization from ether-petroleum ether.

51 G. of rac.-α-{[(3-methoxybenzyl)amino]methyl}-4-nitrobenzyl alcohol hydrochloride are heated to 100° for half an hour with 125 ml. of polyphosphoric acid. After treatment with ice and making alkaline with sodium carbonate, extraction with methylene chloride and evaporation of the organic phase, there are obtained 43 g. of a red-brown oil. Chromatography on 3.5 kg. of silica gel with ether-cyclohexane-diethylamine 40:10:1 yields two pure main fractions which crystallize after treatment with ethanolic hydrogen chloride and ethyl acetate. After recrystallization from methanol-ether, there are obtained 9.9 g. of slightly yellowish rac.-1,2,3,4-tetrahydro-5-methoxy-4-(4-nitrophenyl)isoquinoline hydrochloride, m.p. 260°–261° and 12.5 g. of slightly yellowish rac.-1,2,3,4-tetrahydro-7-methoxy-4-(4-nitrophenyl)isoquinoline hydrochloride, m.p. 225°–226°.

EXAMPLE 10

The free base obtained from 2.0 g. of rac.-1,2,3,4-tetrahydro-7-methoxy-2-methyl-4-(4-nitrophenyl)isoquinoline hydrochloride is hydrogenated in 200 ml.

of methanol with 200 mg. of platinum oxide at room temperature and atmospheric pressure. After treatment with ethanolic hydrogen chloride and recrystallization from methanol-ether, there are obtained 2.1 g. of rac.-4-(4-aminophenyl)-1,2,3,4-tetrahydro-7-methoxy-2-methylisoquinoline dihydrochloride, m.p. 250°–255° (softening at 210°).

EXAMPLE 11

The free base prepared from 4.5 g. of rac.-1,2,3,4-tetrahydro-7-methoxy-2-methyl-4-(4-nitrophenyl)isoquinoline hydrochloride is stirred with 60 ml. of 48% hydrogen bromide solution for 1–½ hours at 150° (bath temperature). After concentration, extraction with ethyl acetate and sodium bicarbonate solution, acidification with ethanolic hydrogen chloride and recrystallization from methanol-ether, there are obtained 4.2 g. of almost colorless rac.-1,2,3,4-tetrahydro-2-methyl-4-(4-nitrophenyl)-7-isoquinolinol hydrochloride, m.p. 263°–265° (dec.).

EXAMPLE 12

The free base obtained from 13.5 g. of rac.-1,2,3,4-tetrahydro-7-methoxy-4-(3-nitrophenyl)isoquinoline hydrochloride is heated for 1 hour at 120° (bath temperature) with 15.9 ml. of formic acid and 16.7 ml. of 35% formaldehyde solution. After concentration, extraction with methylene chloride and sodium bicarbonate solution, acidification with ethanolic hydrogen chloride, crystallization and recrystallization from methanolether, there are obtained 9.5 g. of yellow-grey rac.-1,2,3,4-tetrahydro-7-methoxy-2-methyl-4-(3-nitrophenyl)isoquinoline hydrochloride, m.p. 247°–248° (softening at 238°).

The starting material can be manufactured as follows:

3-Nitroacetophenone is brominated in the $\alpha$-position, the bromination product is reduced by means of sodium borohydride to the corresponding bromohydride and this is treated with ammonia. There is obtained rac.-$\alpha$-(aminomethyl)-3-nitrobenzyl alcohol which melts at 107°–108° (softening from 105°) after crystallization from ethyl acetate-ether.

38.3 G. of rac.-$\alpha$-(aminomethyl)-3-nitrobenzyl alcohol are boiled at reflux with 32.5 g. of 3-methoxybenzaldehyde in 500 ml. of benzene using a water-separator until no more water is formed. After concentration, the mixture is taken up in 1.5 l. of methanol, 20 g. of sodium borohydride are gradually added with stirring and ice-cooling and the mixture is stirred at room temperature for a further 3 hours. Extraction with methylene chloride-water, acidification with ethanolic hydrogen chloride and crystallization and recrystallization from methanol-ether gives 63.8 g. of rac.-$\alpha$-{[(3-methoxybenzyl)amino]methyl}-3-nitrobenzyl alcohol hydrochloride, m.p. 193°–195° (softening at 186°).

55 G. of rac.-$\alpha$-{[(3-methoxybenzyl)amino]methyl}-3-nitrobenzyl alcohol hydrochloride and 165 g. of polyphosphoric acid (84.1% $P_2O_5$) are heated to 100° for 45 minutes. After the addition of a little ice and ethyl acetate the mixture is made alkaline with sodium carbonate and extracted. The ethyl acetate extract (46 g.) is chromatographed on 3.7 kg. of silica gel. With ether-acetone-diethylamine 19:1:1 there are eluted two uniform main fractions of 7.0 g. and 22.2 g. After acidification with ethanolic hydrochloric acid, crystallization and recrystallization from methanol-ether, from the first fraction there is obtained rac.-1,2,3,4-tetrahydro-5-methoxy-4-(3-nitrophenyl)isoquinoline hydrochloride, m.p. 217°–219° and from the second rac.-1,2,3,4-tetrahydro-7-methoxy-4-(3-nitrophenyl)isoquinoline hydrochloride, m.p. 253°–255°.

EXAMPLE 13

The free base obtained from 2.5 g. of rac.-1,2,3,4-tetrahydro-7-methoxy-2-methyl-4-(3-nitrophenyl)isoquinoline hydrochloride is dissolved in 250 ml. of methanol and hydrogenated with 250 mg. of platinum oxide for half an hour. After acidification with ethanolic hydrogen chloride, crystallization with ether and recrystallization from methanol-ether, there are obtained 2.1 g. of rac.-4-(3-aminophenyl)-1,2,3,4-tetrahydro-7-methoxy-2-methylisoquinoline dihydrochloride, m.p. 250°–251°.

EXAMPLE 14

The free base obtained from 4.0 g. of rac.-1,2,3,4-tetrahydro-7-methoxy-2-methyl-4-(3-nitrophenyl)isoquinoline hydrochloride is heated to 150°C. (bath-temperature) for 1.5 hours with 60 ml. of 48% hydrogen bromide solution. After concentration and partitioning between sodium bicarbonate solution and ethyl acetate, acidification with ethanolic hydrogen chloride, crystallization with ether and recrystallization from methanol-ether, there is obtained colorless rac.-1,2,3,4-tetrahydro-2-methyl-4-(3-nitrophenyl)-7-isoquinolinol hydrochloride of melting point 257°–258°C. (dec.).

EXAMPLE 15

The free base obtained from 20.0 g. of rac.-$\alpha$-(aminomethyl)-3,4-dichlorobenzyl alcohol hydrochloride is held at reflux for 1.5 hours in 500 ml. of benzene with 13.7 g. of isovanillin (3-hydroxy-4-methoxybenzaldehyde), the water which separates out being collected by means of a water-separator. After a short time, the resulting imine (m.p. 149°–150°C.) crystallizes out. After evaporation of the benzene, the imine is reduced in 500 ml. of methanol with 10 g. of sodium borohydride at 10°C. After concentration, extraction with methylene chloride and water, acidification with ethanolic hydrogen chloride, crystallization and recrystallization from methanol, there are obtained 24.1 g. of pure rac.-3,4-dichloro-$\alpha$-{[(3-hydroxy-4-methoxybenzyl)amino]methyl}benzyl alcohol hydrochloride of melting point 230°–231°C. The free base melts at 119°–120°C. after recrystallization from ether-petroleum ether.

40 ml. of concentrated sulfuric acid are added with cooling in an ice bath to 14 g. of rac.-3,4-dichloro-$\alpha$-{[(3-hydroxy-4-methoxybenzyl)amino]methyl}benzyl alcohol hydrochloride and the mixture is shaken for 5 minutes. The clear solution is then treated with ice, made alkaline with sodium bicarbonate and extracted with methylene chloride. After acidification with ethanolic hydrogen chloride, there crystallizes a still non-uniform substance which is once more shaken out with ethyl acetate and sodium bicarbonate solution. After acidification and recrystallization from methanol-ether, there are obtained 5.5 g. of pure rac.-4-(3,4-dichlorophenyl)-1,2,3,4-tetrahydro-6-methoxy-7-isoquinolinol hydrochloride of melting point 257°–258°C.

The free base prepared from 3.7 g. of rac.-4-(3,4-dichlorophenyl)-1,2,3,4-tetrahydro-6-methoxy-7-isoquinolinol hydrochloride is treated with 100 ml. of methanol and 5 ml. of 35% formaldehyde solution and, after standing at room temperature for 2 hours, hydrogenated with 5 g. of Raney nickel. After filtration, evaporation and acidification with ethanolic hydrogen chloride, a crystallized product is obtained. Recrystallization from methanol-ether gives rac.-4-(3,4-dichlorophenyl)-1,2,3,4-tetrahydro-6-methoxy-2-methyl-7-isoquinolinol hydrochloride, m.p. 253°–254°C.

EXAMPLE 16

The free base is prepared from 7.0 g. of rac.-α-(aminomethyl)-3,4-dichlorobenzyl alcohol hydrochloride, taken up in 100 ml. of benzene and boiled for an hour with 5.8 g. of veratraldehyde using a water separator. The residue obtained after concentration is taken up in 100 ml. of methanol and reduced at 5°C. with 3 g. of sodium borohydride. After evaporation, solvent extraction, acidification with ethanolic hydrogen chloride and recrystallization from methanol-ether, there are obtained 10.6 g. of rac.-3,4-dichloro-α-{[(3,4-dimethoxybenzyl)amino]methyl}benzyl alcohol hydrochloride, m.p. 209°–210°C. The free base melts at 126°–127°C. after recrystallization from ether-petroleum ether.

At room temperature and with stirring, 9.5 g. of rac.-3,4-dichloro-α-{[(3,4-dimethoxybenzyl)amino]methyl}benzyl alcohol hydrocholride are introduced into 100 ml. of a mixture of equal volumes of concentrated sulfuric acid and water and the mixture is heated at 100°C. for 1 hour. After making alkaline, extracting the base with methylene chloride, acidification with ethanolic hydrogen chloride and recrystallization from methanolethyl acetate, there are obtained 6.5 g. of rac.-4-(3,4-dichlorophenyl)-1,2,3,4-tetrahydro-6,7-dimethoxyisoquinoline hydrochloride, m.p. 247°–248°C. (softening at 240°C.).

The free base released from 6.5 g. of rac.-4-(3,4-dichlorophenyl)-1,2,3,4-tetrahydro-6,7-dimethoxyisoquinoline hydrochloride is heated at 120°C. (bath temperature) for 1 hour with 10 ml. of formic acid and 10 ml. of 35% formalin solution. After evaporation, extraction with sodium carbonate solution and methylene chloride and acidification with ethanolic hydrogen chloride, there is obtained rac.-4-(3,4-dichlorophenyl)-1,2,3,4-tetrahydro-6,7-dimethoxy-2-methylisoquinoline hydrochloride which is recrystallized from methanol-ether and then melts at 243°–246°C. (softening at 238°C). The free base melts at 115°–116°C. after recrystallization from ether-petroleum ether.

EXAMPLE 17

The free bases are prepared from 5.4 g of a mixture of the two diastereoisomers of rac.-4-(3,4-dichlorophenyl)-1,2,3,4-tetrahydro-7-methoxy-1-methylisoquinoline hydrochloride (ratio about 3:2), dissolved in 100 ml. of methanol, allowed to stand at room temperature for 3 hours with 3.6 ml. of 35% formaldehyde solution and thereupon hydrogenated over about 3 g. of Raney nickel. There are obtained 5.4 g. of a yellow oil which is chromatographed on silica gel, two main fractions being eluted with cyclohexane-ether-diethylamine 50:50:1. The first crystallizes with ethanolic hydrogen chloride and either and gives 2.3 g. of the hydrochloride of one of the two diastereomeric rac.-4-(3,4-dichlorophenyl)-1,2,3,4-tetrahydro-7-methoxy-1,2-dimethylisoquinolines, m.p. 253°–255°. The second fraction crystallizes after treatment with citric acid in methanol and yields, after recrystallization from methanol, 2.3 g. of the citrate of the other of the two diastereomeric rac.-4-(3,4-dichlorophenyl)-1,2,3,4-tetrahydro-7-methoxy-1,2-dimethylisoquinolines, m.p. 175°–176°. By extraction of the base from the said citrate, acidification with ethanolic hydrogen chloride and recrystallization from methanol-ether there is obtained the corresponding hydrochloride, m.p. 206°–207°.

The starting material can be manufactured as follows:

The free base obtained from 35.0 g. of rac.-α-(aminomethyl)-3,4-dichlorobenzyl alcohol hydrochloride is heated at reflux for 16 hours with 22.5 g. of 3-methoxyacetophenone in 500 ml. of toluene, water which separates off being collected by means of a water separator. After evaporation, the residue is treated with 400 ml. of methanol, reduced with a total of 10 g. of sodium borohydride with ice cooling and stirred for a further 3 hours at about 15°. After concentration, extraction with methylene chloride and water, treatment with ethanolic hydrogen chloride, crystallization from ethyl acetate-petroleum ether and repeated recrystallization from methanol-ether, there are obtained 18 g. of the hydrochloride of one of the two diastereomeric racemic 3,4-dichloro-α-{[(3-methoxy-α-methylbenzyl)amino]methyl} benzyl alcohols, m.p. 183°–184°. After extraction with methylene chloride and sodium hydroxide solution and treatment with ether, from the mother liquor there crystallize 13.1 g. of the other diastereomer as the free base, m.p. 80°–81°. Its hydrochloride melts at 130°–131° after recrystallization from methanol-ether.

10.4 G. of rac.-3,4-dichloro-α-{[(3-methoxy-α-methylbenzyl)amino]methyl}benzyl alcohol (diastereomer, m.p. 80°–81°) are heated to 100° under nitrogen for 30 minutes in 55 ml. of polyphosphoric acid. The reaction mixture is thereupon poured onto ice and extracted with methylene chloride and 3-N sodium hydroxide. There are obtained 9.9g. of an oily base which is chromatographed on 560 g. of silica gel. Two main fractions are eluted with cyclohexane-ether-diethylamine 25:25:1. After acidification with ethanolic hydrogen chloride, crystallization and recrystallization from methanol-ether, there are obtained 2.5 g. of rac.-4-(3,4-dichlorophenyl)-1,2,3,4-tetrahydro-5-methoxy-1-methylisoquinoline hydrochloride, m.p. 243°–244° and 6.0 g. of rac.-4-(3,4-dichlorophenyl)-1,2,3,4-tetrahydro-7-methoxy-1-methylisoquinoline hydrochloride, m.p. 179°–180°. The base derived from the first product, i.e., rac.-4-(3,4-dichlorophenyl)-1,2,3,4-tetrahydro-5-methoxy-1-methylisoquinoline, displays a m.p. of 70°–71° after recrystallization from ether-petroleum ether.

According to the nuclear resonance spectrum, the first product consists of a mixture of equal parts of two diastereomers and the second product of a diastereomer mixture in the ratio of about 3:2.

EXAMPLE 18

1.00 G. of the hydrochloride of one of the two diastereomeric rac.-3,4-dichloro-α-{[(3-methoxy-α-methylbenzyl)amino]methyl}benzyl alcohols (m.p. 193°–194°) is heated to 100° for half an hour with 5 ml. of polyphosphoric acid. After preparing a basic solution with dilute sodium hydroxide, the product is extracted with methylene chloride, evaporated, dissolved in 20 ml of methanol and allowed to stand for 2 hours with 1 ml of 35% formalin solution. By hydrogenation over 1 g. of Raney nickel there are obtained 950 mg. of an almost colorless oil which, according to thin layer chromatography, consists of two main products and two by-products. Chromatography on 360 g. of silica gel with cyclohexane-ether-diethylamine 50:50:1 yields as a third substance an oil from which, by acidification with ethanolic hydrogen chloride and crystallization with methanol-ether, there are obtained 450 mg. of the hydrochloride of one of the two rac.-4-(3,4-dichlorophenyl)-1,2,3,4-tetrahydro-7-methoxy-1,2-dimethylisoquinolines, m.p. 218°–220°. By dissolving in methanol-ether and seeding with the hydrochloride of m.p. 253°–255° obtained in accordance with Example 17 there is obtained another crystal modification, m.p. 253°–255°.

EXAMPLE 19 a. The free base prepared from 1.25 g. of the rac.-4-(3,4,-dichlorophenyl)-1,2,3,4-tetrahydro-7-methoxy-1,2-dimethylisoquinoline hydrochloride, m.p. 253°–255° (obtained in Example 17) is heated to 150° (bath temperature) for 6 hours with 30 ml. of 48% hydrogen bromide solution. After evaporation and rendering alkaline with sodium bicarbonate extraction with methylene chloride, acidification with ethanolic hydrogen chloride, crystallization with ethyl acetate and recrystallization from methanol-ether, there are obtained 1.1 g. of the hydrochloride of one of the two diastereomeric rac.-4-(3,4-dichlorophenyl)-1,2,3,4-tetrahydro-1,2-dimethyl-7-isoquinolinols, m.p. 254°–255°. Extraction with sodium bicarbonate and methylene chloride yields the corresponding free base, m.p. 180°.

b. The free base prepared from 750 mg. of the rac.-4-(3,4-dichlorophenyl)-1,2,3,4-tetrahydro-7-methoxy-1,2-dimethylisoquinoline hydrochloride, m.p. 206°–207° (obtained in Example 17) is heated to 150° (bath temperature) for an hour with 10 ml. of 48% hydrogen bromide solution. After evaporation, extraction with methylene chloride and saturated sodium bicarbonate solution, evaporation, acidification with ethanolic hydrochloric acid, crystallization with ethyl acetate and recrystallization from methanol-ether, there are obtained 710 mg. of the hydrochloride of the other of the two diastereomeric rac.-4-(3,4-dichlorophenyl)-1,2,3,4-tetrahydro-1,2-dimethyl-7-isoquinolinols, m.p. 254°–255°. The free base obtained by extraction with methylene chloride and sodium bicarbonate displays a m.p. of 219°–220° after recrystallization from ether-petroleum ether.

EXAMPLE 20

The free base obtained from 3.1 g. of rac.-4-(3,4,-dichlorophenyl)-1,2,3,4-tetrahydro-6,7-dimethoxy-2-methylisoquinoline hydrochloride by partitioning between methylene chloride and sodium hydroxide solution is heated at reflux in 100 ml. of 48% hydrobromic acid at a bath temperature of 160° C. for 2 hours. Crystallization, accompanied by strong foaming, begins after half an hour. After cooling, the resulting mixture is treated with about 80 ml. of water and the solid is filtered off and recrystallized from methanol-ether to yield 2.6 g. of rac.-4-(3,4-dichlorophenyl)-1,2,3,4-tetrahydro-2-methyl-6,7-isoquinolinediol hydrobromide, m.p. 285°–286° C.

EXAMPLE 21

4.5 g. of rac.-3,4-dichloro-α-{[(3-methoxybenzyl)amino]methyl}benzyl alcohol in 100 ml. of methanol and 2.5 ml. of 35% formaldehyde solution are allowed to stand at room temperature for 1 hour and thereafter hydrogenated with Raney nickel. Catalyst is subsequently filtered off with the aid of diatomaceous earth and the filtrate concentrated in vacuo. The residue is dissolved in ether and the solution dried over sodium sulfate and concentrated. The residue is treated with ethanolic hydrochloric acid and crystallized and recrystallized from methanol-ether to yield 5.1 g. of colorless rac.-3,4-dichloro-α-{[(m-methoxybenzyl)methylamino]methyl}benzyl alcohol hydrochloride, m.p. 166°–167° C.

1.50 g. of rac.-3,4-dichloro-α-{[(3-methoxybenzyl)methylamino]methyl}benzyl alcohol hydrochloride are dissolved with swirling in 20 ml. of a mixture of 1 part by volume of concentrated sulfuric acid and 1 part by volume of water and the solution is heated for 1.5 hours at a bath temperature of 100° C., then basified with 3N sodium hydroxide solution while cooling with ice and extracted with chloroform. The extract is dried over sodium sulfate and evaporated in vacuo. The residual base mixture is chromatographed on 60 g. of silica gel (0.05–0.20 mm) in chloroform-diethylamine 99:1. There are successively eluted two thin layer chromatographically uniform substances which crystallize in ethyl acetate after acidification with ethanolic hydrochloric acid. After recrystallization from methanol-ether there are obtained colorless rac.-4-(3,4-dichlorophenyl)-1,2,3,4-tetrahydro-5-methoxy-2-methylisoquinoline hydrochloride, m.p. 264°–265° C. and colorless rac.-4-(3,4-dichlorophenyl)-1,2,3,4-tetrahydro-7-methoxy-2-methylisoquinoline hydrochloride, m.p. 273°–275° C

EXAMPLE 22

500 mg. of rac.-4-(3,4-dichlorophenyl)-1,2,3,4-tetrahydro-7-methoxyisoquinoline hydrochloride are heated at reflux in 10 ml. of 48% hydrogen bromide solution for 2 hours under nitrogen at a bath temperature of 150°. The resulting mixture is evaporated in vacuo and the residue partitioned between chloroform-ethyl acetate 9:1 and saturated sodium bicarbonate solution. The organic phase is dried and concentrated to yield 300 mg. of colorless rac.-4-(3,4-dichlorophenyl)-1,2,3,4-tetrahydro-7-isoquinolinol, m.p. 243°–244° C. By acidification with ethanolic hydrogen chloride and crystallization and recrystallization from methanol-ether there is obtained the corresponding hydrochloride, m.p. 270°–272° C.

The free base is isolated from 500 mg. of rac.-4-(3,4-dichlorophenyl)-1,2,3,4-tetrahydro-7-isoquinolinol hydrochloride by partitioning between chloroform-ethyl acetate 9:1 and sodium bicarbonate solution. The base is dissolved in 15 ml. of methanol and the solution is treated with 0.75 ml. of 35% formaldehyde solution, allowed to stand at room temperature for 2 hours and hydrogenated with 1 g. of Raney nickel. Catalyst is subsequently filtered off and the filtrate is evaporated. The residue is acidified with ethanolic hydrogen chloride and crystallized and recrystallized from methanol-ether to give colorless rac.-4-(3,4-dichlorophenyl)-1,2,3,4-tetrahydro-2-methyl-7-isoquinolinol hydrochloride, m.p. 287°–288° C. (with decomposition, sintering at 280° C.).

EXAMPLE 23

10.0 g. of rac.-4-(3,4-dichlorophenyl)-1,2,3,4-tetrahydro-7-methoxyisoquinoline hydrochloride are treated with 100 ml. of ethanol aand heated at reflux for 3 hours at a bath temperature of 100° C. with 4 g. of solid sodium hydroxide and 12 g. of ethyl bromide. The resulting mixture is concentrated in vacuo and the residue is partitioned between methylene chloride and 3N sodium hydroxide solution. The organic layer is dried over sodium sulfate and concentrated. The residual base is treated with ethanolic hydrochloric acid and crystallized and recrystallized from methanol to yield 9.5 g. of colorless rac.-4-(3,4-dichlorophenyl)-2-ethyl-1,2,3,4-tetrahydro-7-methoxyisoquinoline hydrochloride, m.p. 269°–270° C. (sintering at 267° C.).

EXAMPLE 24

The free base is isolated from 4.50 g. of rac.-4-(3,4-dichlorophenyl)-2-ethyl-1,2,3,4-tetrahydro-7-methoxyisoquinoline hydrochloride by partitioning between chloroform and saturated sodium bicarbonate solution. After the addition of 100 ml. of 48% hydrobromic acid (a precipitate of the hydrobromide immediately forms), the mixture is heated at reflux with stirring for 4 hours at a bath temperature of 160° C. The resulting mixture is partitioned between 500 ml. of chloroform and 300 ml. of saturated sodium bicarbonate solution. This organic phase is separated off, dried over sodium sulfate and evaporated in vacuo. The residue is acidified with ethanolic hydrochloric acid, crystallized with ethanol-ether and recrystallized from methanol to yield 3.0 g. of colorless rac.-4-(3,4-dichlorophenyl)-2-ethyl-1,2,3,4-tetrahydro-7-isoquinolinol hydrochloride, m.p. 305°–307° C. (sintering at 260° C.).

EXAMPLE 25

The free base is isolated from 500 mg. of rac.-4-(3,4-dichlorophenyl)-1,2,3,4-tetrahydro-7-methoxyisoquinoline hydrochloride by partitioning between chloroform and saturated sodium bicarbonate solution. It is heated at 150° C. for 3 hours in an autoclave together with 5 ml. of isopropyl bromide and 200 mg. of finely ground sodium carbonate. The resulting mixture is concentrated and the residue is partitioned between chloroform and 3N sodium hydroxide solution. The organic phase is separated off, dried and evaporated. The residue is acidified with dilute hydrochloric acid and crystallized and recrystallized from methanol to yield 300 mg. of colorless rac.-4-(3,4-dichlorophenyl)-2-isopropyl-1,2,3,4-tetrahydro-7-methoxyisoquinoline hydrochloride, m.p. 240°–241° C.

EXAMPLE 26

500 mg. of rac.-4-(3,4-dichlorophenyl)-2-isopropyl-1,2,3,4-tetrahydro-7-methoxyisoquinoline hydrochloride in 10 ml. of 48% hydrobromic acid are heated under reflux under nitrogen for 2 hours at a bath temperature of 160° C. The resulting mixture is evaporated in vacuo and the residue is partitioned between chloroform and sodium carbonate solution. The organic layer is separated off and evaporated. The residue is crystallized with petroleum ether and recrystallized from ether-petroleum ether to yield 300 mg. of colorless rac.-4-(3,4-dichlorophenyl)-2-isopropyl-1,2,3,4-tetrahydro-7-isoquinolinol, m.p. 155°–156° C. Acidification with dilute hydrochloric acid, crystallization and recrystallization from methanol-ether yield the corresponding hydrochloride as colorless crystals, m.p. 274°–277° C. (dec.).

EXAMPLE 27

500 mg. of rac.-4-(3,4-dichlorophenyl)-1,2,3,4-tetrahydro-7-methoxyisoquinoline hydrochloride in 20 ml. of ethanol are shaken at room temperature for 0.75 hour with 200 mg. of solid sodium hydroxide and 5 ml. of benzyl bromide. The resulting mixture is concentrated in vacuo and the residue is partitioned between chloroform and 3N sodium hydroxide solution. The organic phase is separated off, dried and evaporated. The residue is acidified with ethanolic hydrogen chloride and the resulting salt is crystallized from chloroform-ether to yield colorless crystals which are recrystallized from ethanol to give 400 mg. of rac.-2-benzyl-4-(3,4-dichlorophenyl)-1,2,3,4-tetrahydro-7-methoxyisoquinoline hydrochloride of melting point 263°–264° C. (sintering at 245° C.).

EXAMPLE 28

Tablets each containing 25.0 mg. of 4-(3,4-dichlorophenyl)-1,2,3,4-tetrahydro-7-methoxy-2-methylisoquinoline hydrochloride, 139.0 mg. of corn starch, 35.0 mg. of lactose and 1.0 mg. of magnesium stearate and each having a total weight of 200.0 mg. are prepared by granulating a mixture of the 4-(3,4-dichlorophenyl)-1,2,3,4-tetrahydro-7-methoxy-2-methylisoquinoline hydrochloride and the lactose with a paste prepared from part of the corn starch, drying, adding a mixture of the remainder of the corn starch and the magnesium stearate, and compressing the resulting mixture on a tabletting machine at a tablet weight of 200 mg. The resulting tablets can be subsequently coated with ethylcellulose and polyethylene glycol.

Tablets each containing 10.0 mg. of 4-(3,4-dichlorophenyl)-1,2,3,4-tetrahydro-7-methoxy-2-methylisoquinoline hydrochloride, 136.0 mg. of corn starch, 50.0 mg. of lactose, 3.4 mg. of talc and 0.6 mg. of magnesium stearate and each having a total weight of 200.0 mg. are prepared in a similar manner, the talc being added at the same time as the corn starch/magnesium stearate mixture.

EXAMPLE 29

Suppositories each containing 0.010 g. of 4-(3,4-dichlorophenyl)-1,2,3,4-tetrahydro-7-methoxy-2-methylisoquinoline hydrochloride, 1.245 g. of cocoa butter (m.p. = 36°–37° C.) and 0.045 g. of carnauba wax and each having a total weight of 1.3 g. are prepared by melting cocoa butter and carnauba wax in a glass or steel vessel of suitable size, thoroughly mixing, cooling, adding 4-(3,4-dichlorophenyl)-1,2,3,4-tetrahydro-7-methoxy-2-methylisoquinoline hydrochloride, stirring until complete and uniform dispersion is obtained and pouring the mixture into suppository molds which give suppositories each weighing 1.3 g. After cooling, the suppositories are taken from the molds and individually wrapped in waxed paper or metal foil.

EXAMPLE 30

Capsules each containing 10 mg. of 4-(3,4-dichlorophenyl)-1,2,3,4-tetrahydro-7-methylisoquinoline hydrochloride, 165mg. of lactose, 30 mg. of corn starch and 5 mg. of talc and each having a total net weight of 210 mg. are prepared by mixing 4-(3,4-dichlorophenyl)-1,2,3,4-tetrahydro-7-methoxy-2-methylisoquinoline hydrochloride, lactose and corn starch, firstly in a mixer then in a comminuting machine, returning the mixed powder to the mixer, adding talc, mixing thoroughly and filling the mixture into hard gelatin capsules on a capsulating machine.

EXAMPLE 31

10,000 ml. of an injection solution containing, per ml., 25.0 mg. of 4-(3,4-dichlorophenyl)-1,2,3,4-tetrahydro-7-methoxy-2-methylisoquinoline hydrochloride, 0.4 ml. of propylene glycol, 0.015 ml. of benzaldehyde-free benzyl alcohol, 0.10 ml. of 95% ethanol, 48.8 mg. of sodium benzoate, 1.2 mg. of benzoic acid and water for injection q.s. to 1 ml. are prepared by dissolving 250 mg. of 4-(3,4-dichlorophenyl)-1,2,3,4-tetrahydro-7-methoxy-2-methylisoquinoline hydrochloride in 150 ml. of benzyl alcohol, adding 4,000 ml. of propylene glycol and 1,000 ml. of ethanol, dissolving 12 g. of benzoic acid in the resulting mixture, adding a solution of 488 g. of sodium benzoate in 3,000 ml. of water and making up to a volume of 10,000 ml. with water. The resulting solution is filtered and filled into ampules of a suitable size. The unfilled space in the ampules is fitted with nitrogen, then the ampules are sealed and sterilized in an autoclave at 0.7 atm. for 0.5 hour.

EXAMPLE 32

Tablets, suppositories, capsules or injection solutions are prepared in accordance with the data of Example 28, 29, 30, or 31, respectively, but instead of 4-(3,4-dichlorophenyl)-1,2,3,4-tetrahydro-7-methoxy-2-methylisoquinoline hydrochloride there is used 4-(3,4-dichlorophenyl)-1,2,3,4-tetrahydro-2-methyl-7-isoquinolinol hydrochloride or 4-(4-chlorophenyl)-1,2,3,4-tetrahydro-2-methyl-7-isoquinolinol hydrochloride.

I claim:
1. A compound of the formula

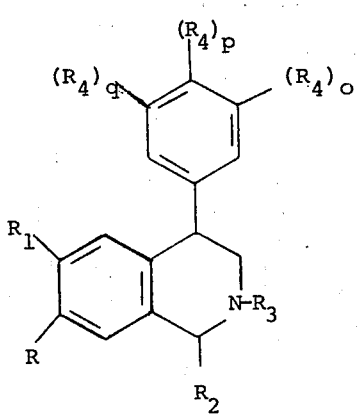

wherein R signifies hydroxy or lower alkoxy, $R_1$ signifies hydrogen, $R_2$ signifies hydrogen, $R_3$ signifies lower alkyl, $R_4$ signifies chlorine and $o$, $p$ and $q$ are the integers 0 or 1, wherein one or two of the characters $o$, $p$ or $q$ is the integer 0.

2. A compound of claim 1 wherein R signifies hydroxy, $R_1$ and $R_2$ signify hydrogen, $R_3$ signifies methyl and $R_4$ signifies chlorine.

3. The compound of claim 2 wherein $q$ and $o$ are 0 and $p$ is 1, i.e., a compound of the formula 4-(4-chlorophenyl)-1,2,3,4-tetrahydro-2-methyl-7-isoquinolinol.

4. The compound wherein $q$ is 0 and $p$ and $o$ are 1, i.e., a compound of the formula 4-(3,4-dichlorophenyl)-1,2,3,4-tetrahydro-2-methyl-7-isoquinolinol.

5. The compound of claim 2 wherein $q$ and $p$ are 0 and $o$ is 1, i.e., a compound of the formula 4-(3-chlorophenyl)-1,2,3,4-tetrahydro-2-methyl-7-isoquinolinol.

6. A compound of claim 1 wherein R signifies methoxy, $R_1$ and $R_2$ signify hydrogen, $R_3$ signifies methyl and $R_4$ signifies chlorine 7. The compound of claim 6 wherein $q$ and $o$ are 0 and $p$ is 1, i.e., a compound of the formula 4-(4-chlorophenyl)-1,2,3,4-tetrahydro 7-methoxy-2-methylisoquinoline.

8. The compound wherein $q$ is 0 and $p$ and $o$ are 1, i.e., a compound of the formula 4-(3,4-dichlorophenyl)-1,2,3,4-tetrahydro-7-methoxy-2-methylisoquinoline.

9. The compound of claim 6 wherein $q$ and $p$ are 0 and $o$ is 1, i.e., a compound of the formula 4-(3-chlorophenyl)-1,2,3,4-tetrahydro-7-methoxy-2-methylisoquinoline.

10. A compound of claim 1 wherein $R_1$ and $R_2$ are hydrogen and $R_3$ is lower alkyl.

11. The compound wherein R is methoxy, the lower alkyl group as $R_3$ is ethyl, $R_4$ is chlorine and $q$ is 0 and $p$ and $o$ are 1, i.e., a compound of the formula 4-(3,4-dichlorophenyl)-2-ethyl-1,2,3,4-tetrahydro-7-methoxyisoquinoline.

12. The compound wherein R is hydroxy, the lower alkyl group as $R_3$ is ethyl, $R_4$ is chlorine and $q$ is 0 and $p$ and $o$ are 1, i.e., a compound of the formula 4-(3,4-dichlorophenyl)-2-ethyl-1,2,3,4-tetrahydro-7-isoquinolinol.

13. The compound wherein R is methoxy, the lower alkyl group as $R_3$ is isopropyl, $R_4$ is chlorine and $q$ is 0 and $p$ and $o$ are 1, i.e., a compound of the formula 4-(3,4-dichlorophenyl)-2-isopropyl-1,2,3,4-tetrahydro-7-methoxyisoquinoline.

14. The compound wherein R is hydroxy, the lower alkyl group as $R_3$ isopropyl, $R_4$ is chlorine and $q$ is 0 and $p$ and $o$ are 1, i.e., a compound of the formula 4-(3,4-dichlorophenyl)-2-isopropyl-1,2,3,4-tetrahydro-7-isoquinolinol.

* * * * *

UNITED STATES PATENT OFFICE
CERTIFICATE OF CORRECTION

Patent No. 3,947,456          Dated March 30, 1976

Inventor(s) Alfred Rheiner

It is certified that error appears in the above-identified patent and that said Letters Patent are hereby corrected as shown below:

Column 28, claim 14, line 53, after "$R_3$" please insert the word is.

Signed and Sealed this

Thirty-first Day of August 1976

[SEAL]

Attest:

RUTH C. MASON
*Attesting Officer*

C. MARSHALL DANN
*Commissioner of Patents and Trademarks*